(12) United States Patent
Holtby et al.

(10) Patent No.: US 6,966,893 B2
(45) Date of Patent: Nov. 22, 2005

(54) OVER PRESSURIZATION RELIEF APPARATUS

(75) Inventors: Troy Holtby, Bluffdale, UT (US); Greg McArthur, Sandy, UT (US); Tom Stout, Salt Lake City, UT (US); Arlin Dale Nelson, Sandy, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 164 days.

(21) Appl. No.: 10/649,001

(22) Filed: Aug. 26, 2003

(65) Prior Publication Data

US 2005/0049548 A1   Mar. 3, 2005

(51) Int. Cl.[7] .......................... A61M 1/00; A61M 5/00
(52) U.S. Cl. ..................... 604/146; 604/118; 604/249
(58) Field of Search ............................... 604/141, 142, 604/146, 118, 65, 186, 246, 247, 249; 128/DIG. 12; 222/95, 396, 397, 402.2

(56) References Cited

U.S. PATENT DOCUMENTS

| | | | |
|---|---|---|---|
| 4,469,099 A | | 9/1984 | McEwen |
| 4,566,462 A | | 1/1986 | Janssen |
| 4,657,160 A | * | 4/1987 | Woods et al. .................. 222/94 |
| 5,053,012 A | * | 10/1991 | Edwards et al. ............. 604/146 |
| 5,059,182 A | * | 10/1991 | Laing .......................... 604/142 |
| 5,749,854 A | * | 5/1998 | Shen ........................... 604/131 |
| 5,766,130 A | | 6/1998 | Selmonosky |
| 5,954,696 A | * | 9/1999 | Ryan ........................... 604/141 |
| 6,299,629 B1 | | 10/2001 | Gruenfeld et al. |
| 6,491,638 B2 | | 12/2002 | Oka |
| 6,800,069 B2 | * | 10/2004 | Lampropoulos et al. ..... 604/140 |
| 2004/0167471 A1 | * | 8/2004 | Lampropoulos et al. ..... 604/140 |

* cited by examiner

Primary Examiner—Sharon Kennedy
(74) Attorney, Agent, or Firm—Workman Nydegger

(57) ABSTRACT

An over pressurization relief apparatus having a manual over pressurization selector which allows a user to manually select from at least a first and second over pressurization limit. The over pressurization relief apparatus includes a pressurization chamber, a pressure relief mechanism, a seal, and a manual over pressurization selector. The pressurization of the pressurization chamber corresponds with the pressurization of the pressure infusion bag. The pressure relief mechanism prevents additional pressurization of the pressure infusion bag once the over pressurization limit has been reached. The seal is positioned between the pressurization chamber and the pressure relief mechanism to prevent the loss of pressurization from the pressure infusion bag when the pressurization in the pressurization chamber is less than the over pressurization limit.

15 Claims, 6 Drawing Sheets

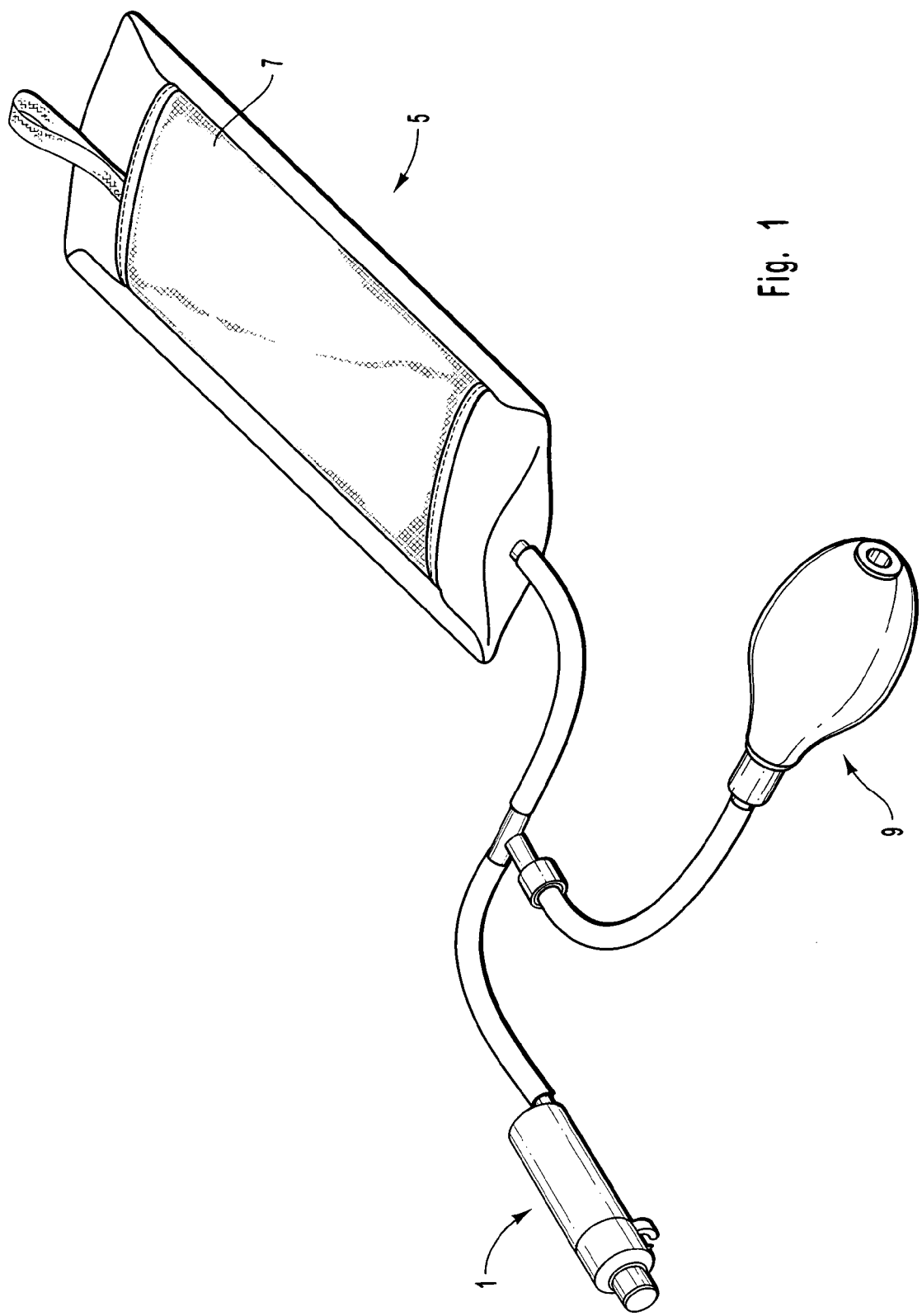

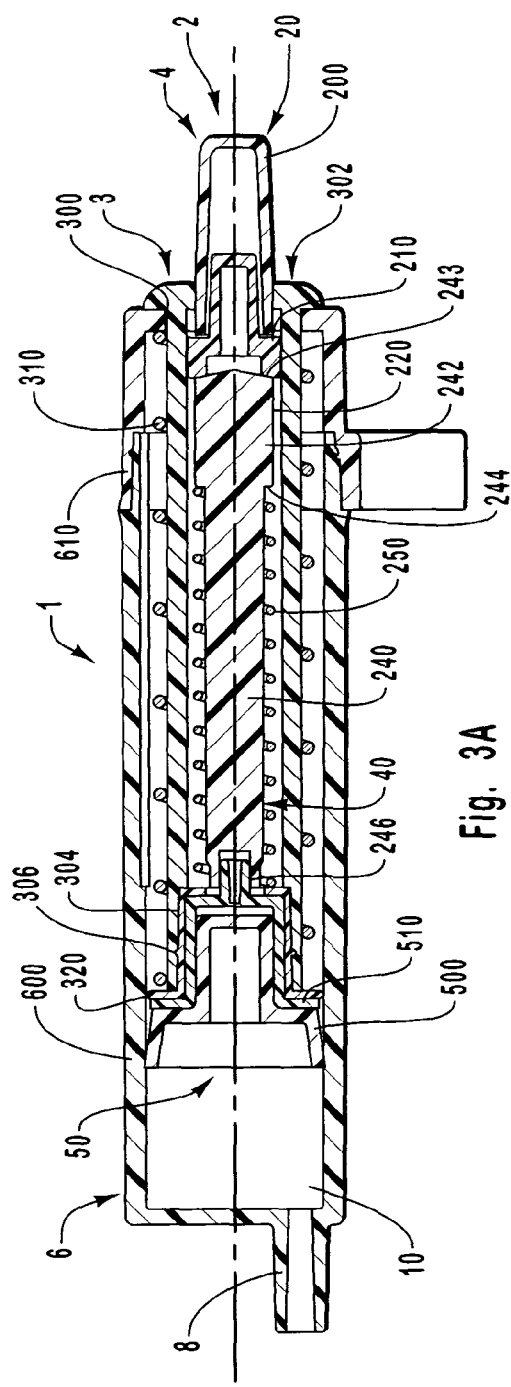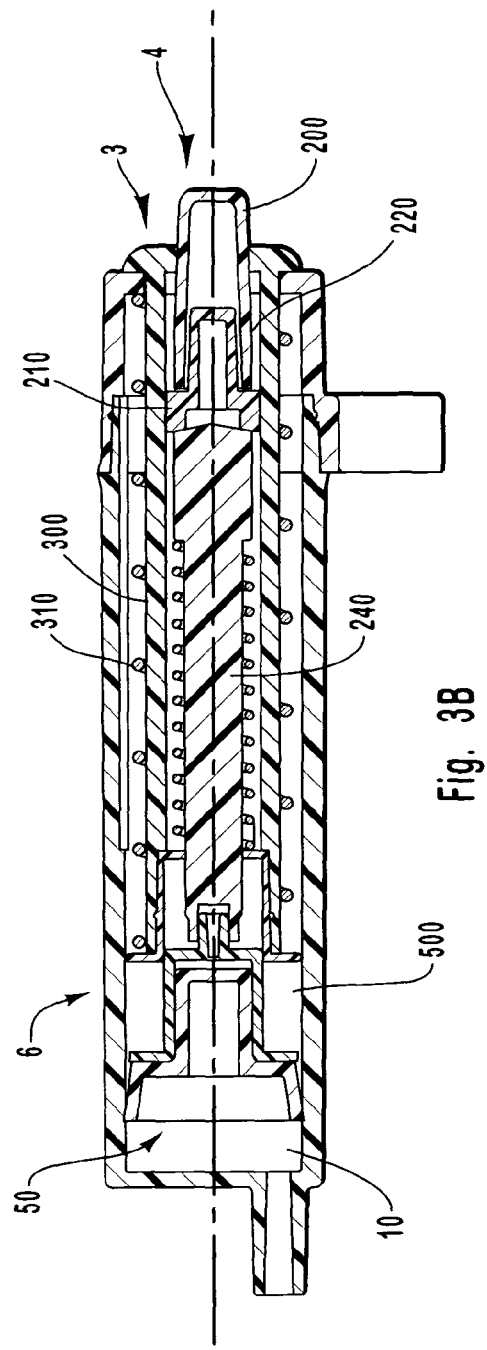

OVER PRESSURIZATION RELIEF APPARATUS

BACKGROUND OF THE INVENTION

1. The Field of the Invention

The present invention relates to over pressurization valves to prevent over pressurization of a pressure infusion bag. In particular, the present invention relates to an over pressurization valve allowing a user to manually select from at least a first and second over pressurization limit.

2. The Relevant Technology

Infusion devices are used for the subcutaneous administration, to humans or animals, of intravenous fluids such as blood, nutrients, medicine or saline. The fluids are stored and administered from pliant infusate bags typically made from plastic film materials. The infusate bags facilitate the administration of infusate fluids, while limiting the amount of air that is transferred to the patient with the fluid.

Infusion devices allow fluids to be administered to patients in a variety of manners. A common administration technique involves suspending an infusate bag from a hook or peg and allowing gravity to provide the force needed to deliver the fluid to the patient by the means of a delivery line. Where suspension administration is utilized, the infusate bag includes an outlet tube at the lower end of the bag. A delivery tube is attached to the outlet tube for delivering the fluid from the bag to the patient. The delivery tube usually includes an observable drop-feed device and an adjustable flow delivery valve for allowing medical staff to regulate the fluid flow rate.

There are limitations to using suspension to administer IV fluids. Where gravitational forces are the sole means of administering fluid, the viscosity of some fluids such as blood and plasma, makes delivery of the fluids problematic. The problem is exacerbated where the fluid must be delivered quickly and efficiently, as with major traumas where large amounts of blood are required in a short amount of time. To facilitate a higher rate of infusate delivery, such as is required with high viscosity fluids, medical staff utilize various methods to increase the pressure on the infusate fluid. Examples of such methods include, pressure pumps, inflation cuffs, inflation bladders, or even manual compression of the infusate bag. Pressure pumps, inflation cuffs, inflation bladders, and manual compression of the infusate bags also allow fluids to be delivered to the patient as needed during ambulation of the patient.

Among the methods of providing compression of the infusate bag, pressure infusion bags have been accepted in the medical products industry as an effective and inexpensive method for providing the pressure required by highly viscous fluids, ambulation, and many other circumstances. Pressure infusion bags comprise an inflatable air bladder with a sleeve or pouch for holding the infusate bag. When the user inflates the air bladder, pressure is exherted on the infusate bag contained in the sleeve, thus providing the pressure needed to deliver the fluid.

An over pressurization valve is often utilized in connection with the pressure infusion bag to prevent additional pressurization of the pressure infusion bag once a desired pressurization has been reached. Typically, the over pressurization valve is configured to prevent rupturing of the pressure infusion bag. However, the over pressurization limit can also correspond with a desired rate of infusate delivery.

One problem associated with over pressurization valves is that a single over pressurization limit is provided by the over pressurization valves. Different over pressurization limits may be desired for different types of infusate, in different types of clinical settings, and/or for different types of procedures. For example, an over pressurization limit recommended to provide a desired delivery rate for medications can be different from the over pressurization limit needed to accommodate the desired delivery rate for blood or plasma. Additionally, the over pressurization limit for providing a desired delivery rate for blood for routine procedures may be insufficient to provide the delivery rate desired in trauma and major surgical settings.

BRIEF SUMMARY OF THE INVENTION

The present invention is directed to an over pressurization relief apparatus configured to prevent over pressurization of a pressure infusion bag. The over pressurization relief apparatus prevents additional pressurization of pressure infusion bag once an over pressurization limit has been reached. The over pressurization relief apparatus includes a manual over pressurization selector which allows a user to manually select from at least a first and second over pressurization limit. This allows a user to select an over pressurization limit to meet the needs of the infusate to be infused into the patient, the procedure to be performed by the practitioner, and/or other parameters related to infusion of an infusate.

According to one aspect of the present invention, the over pressurization relief apparatus includes a pressurization chamber, a pressure relief mechanism, a seal, and a manual over pressurization selector. The pressurization chamber is linked to the pressure infusion bag such that the pressurization in the pressurization chamber corresponds with pressurization in the pressure infusion bag. The pressure relief mechanism prevents additional pressurization of the pressure infusion bag once the over pressurization limit has been reached. The seal is positioned between the pressurization chamber and the pressure relief mechanism to prevent the loss of pressurization from the pressure infusion bag when the pressurization in the pressurization chamber is less than the over pressurization limit. According to one aspect of the present invention, the over pressurization relief apparatus allows the user to quickly and efficiently toggle between a first and second over pressurization limit by depressing a plunger of the manual over pressurization selector.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 1 illustrates an over pressurization relief apparatus and the operating environment in which the over pressurization relief apparatus is utilized.

FIG. 3A is a cross-sectional side view of the over pressurization relief apparatus illustrating the internal components of the over pressurization relief apparatus.

FIG. 3B is a cross-sectional side view of the over pressurization relief apparatus in which the plunger of the over pressurization relief apparatus is depressed to select a second over pressurization limit.

DETAILED DESCRIPTION OF THE PREFERRED EMBODIMENTS

Figure 2A:
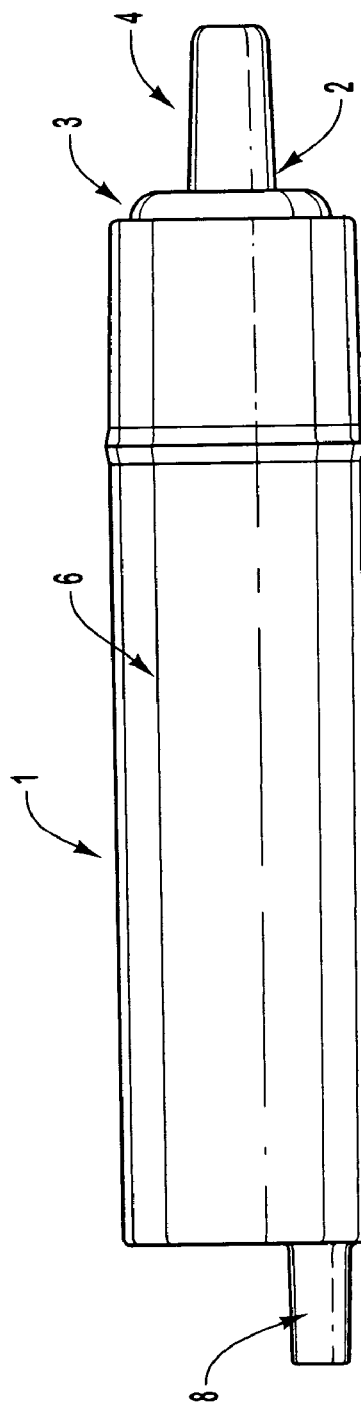
FIG. 2A illustrates the over pressurization relief apparatus where the pressurization in the pressure infusion bag is less than the over pressurization limit.

The present invention is directed to an over pressurization relief apparatus 1 configured to prevent over pressurization of a pressure infusion bag 5. Over pressurization relief apparatus 1 allows a user to select an over pressurization limit to meet the needs of the infusate to be infused into the patient, the procedure to be performed by the practitioner, and/or other parameters related to infusion of an infusate.

According to one aspect of the present invention, over pressurization relief apparatus 1 includes a pressurization chamber 10, a pressure relief mechanism, a seal 500, and a manual over pressurization selector 4. Pressurization chamber 10 is linked to pressure infusion bag 5 such that the pressurization in pressurization chamber 10 corresponds with pressurization in pressure infusion bag 5. Pressure relief mechanism 306 prevents additional pressurization of pressure infusion bag 5 once the over pressurization limit has been reached. Seal 500 is positioned between pressurization chamber 10 and the pressure relief mechanism to prevent the loss of pressurization from pressure infusion bag 5 when the pressurization in pressurization chamber 10 is less than the over pressurization limit. According to one aspect of the present invention, over pressurization relief apparatus 1 allows the user to quickly and efficiently toggle between a first and second over pressurization limit by depressing a plunger of the manual over pressurization selector 4.

FIG. 1 illustrates an over pressure relief apparatus 1 and the operating environment in which over pressure relief apparatus 1 is utilized according to one aspect of the present invention. In the illustrated embodiment, over pressurization relief apparatus 1 is utilized with a pressure infusion bag 5 and a compression bulb 9. Pressure infusion bag 5 is designed to exert pressure on an infusate bag containing fluids to be infused into a patient, such as blood, saline, pharmaceuticals, or the like. The infusate bag is positioned in infusate pouch 7 of pressure infusion bag 5 such that when pressure infusion bag 5 is inflated, pressure is exerted on the infusate bag to facilitate delivery of the infusate to the patient.

Pressure infusion bag 5 is inflated utilizing compression bulb 9. A variety of types and configurations of compression bulbs are known in the medical products industry. Typically such compression bulbs include two one-way valves permitting the infusate bag to be inflated utilizing quick and successive compressions of compression bulb 9. As the client inflates pressure infusion bag 5 the air pressure in the pressure infusion bag 5 increases. Over pressure relief apparatus 1 is configured to prevent over pressurization of pressure infusion bag 5. In the illustrated embodiment, over pressure relief apparatus 1 is in fluid communication with pressure infusion bag 5. When the pressurization in pressure infusion bag 5 exceeds the desired pressurization limit, the pressurization in pressure infusion bag 5 is automatically exhausted to maintain a desired pressurization. This allows the user to quickly and efficiently inflate pressure infusion bag 5 to an over pressurization limit without needing to monitor the actual pressurization in pressure infusion bag 5.

Over pressure relief apparatus 1 includes a manual over pressurization selector which allows the user to manually select from more than one over pressurization limit. By allowing the user to manually select from more than one over pressurization limit the user can tailor the over pressurization limit utilized to the type of procedure to be performed. For example, a lower over pressurization limit can be selected for the administration of medications. A higher over pressurization limit can be selected for the administration of blood in a trauma situation. According to one embodiment of the present invention, the manual over pressurization selector allows the user to select from a first over pressurization limit and a second over pressurization limit. According to another embodiment of the present invention, the manual over pressurization selector allows the user to select from more than two over pressurization limits.

In the illustrated embodiment, over pressurization relief apparatus 1, pressure infusion bag 5, and compression bulb 9 are linked together by pneumatic tubing. As will be appreciated by those skilled in the art, a variety of types and configurations of pressure infusion bags, inflation mechanisms, and methods of connecting over pressurization relief apparatus to the pressure infusion bag can be utilized. For example, in one embodiment, pressure infusion bag utilizes a medium other than ambient air to exert pressure on an infusate bag. In another embodiment, the over pressurization relief apparatus 1 is integrally coupled to the pressure infusion bag. In yet another embodiment, the over pressurization relief apparatus and an inflation mechanism comprise a single apparatus.

FIG. 2A illustrates over pressurization relief apparatus 1 in greater detail according to one aspect of the present invention. In the illustrated embodiment, over pressurization relief apparatus 1 comprises a valve mechanism 2, an outer housing 6, tube engagement port 8, and a pressurization chamber (not shown). Valve mechanism 2 is positioned internal to outer housing 6. Valve mechanism 2 provides a mechanism for preventing over pressurization of the pressure infusion bag, while also allowing the user to manually select from at least a first and second over pressurization limit. In the illustrated embodiment, valve mechanism 2 comprises a pressure responsive mechanism 3 and an over pressurization limit selector 4. Pressure responsive mechanism 3 operates based on the amount of pressurization in pressure infusion bag 5.

Over pressurization limit selector 4 is coupled to pressure responsive mechanism 3. Over pressurization limit selector 4 allows a user to manually select from at least a first and second over pressurization limit such that when the pressurization in the pressure infusion bag exceeds the selected pressurization limit, the air in the pressure infusion bag is exhausted utilizing a pressure relief mechanism. In the illustrated embodiment, the configuration of over pressurization limit selector 4 allows the user to select the first or second over pressurization limit with a quick and simple depression of the plunger of over pressurization limit selector 4. By depressing the plunger the user can quickly and efficiently toggle between at least the first and second predetermined over pressurization limit.

In the illustrated embodiment, over pressurization limit selector 4 is in a first position indicative of a first selected over pressurization limit. Pressure responsive mechanism 3, is also positioned in a first position indicative of a low pressurization in the pressure infusion bag and pressurization chamber. Operation of the over pressurization relief apparatus 1 and response to different pressurizations of the pressure infusion bag are depicted with reference to FIGS. 2B and 2C.

Outer housing 6 is positioned external to other components of over pressurization relief apparatus 1. Additionally, outer housing 6 provides a mechanism for protecting the internal components of over pressurization relief apparatus 1. Over pressurization relief apparatus 1 further includes a tube engagement port 8. Tube engagement port 8 facilitates coupling of pneumatic tubing linking over pressurization relief apparatus 1 with the pressure infusion bag. In the illustrated embodiment, the tube engagement port 8 is integrally coupled with outer housing 6.

Figure 2B:
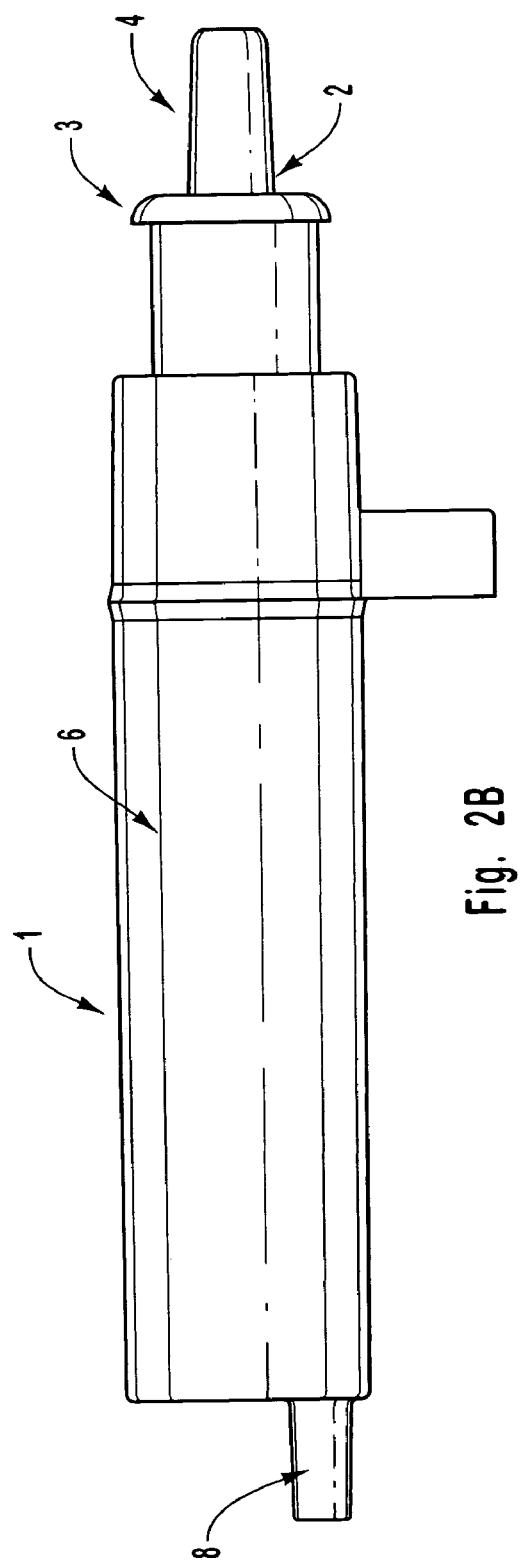
FIG. 2B illustrates the over pressurization relief apparatus where the pressurization in the pressure infusion bag has reached a first over pressurization limit.

With reference now to FIG. 2B, there is shown an over pressurization relief apparatus 1 in which the pressure in the pressure infusion bag has reached a first over pressurization limit. In the illustrated embodiment, over pressurization limit selector 4 is in the first position indicative of the first over pressurization limit as also shown in FIG. 2A. Pressure responsive mechanism 3 is in a second position in which pressure responsive mechanism 3 is extended from outer housing 6. The second position of pressure responsive mechanism 3 results from a high pressurization in pressure infusion bag 5 corresponding with a first over pressurization limit. When moved to the second position, pressure responsive mechanism 3 exhausts air being pumped into the pressure infusion bag that would otherwise result in a pressurization exceeding the over pressurization limit. In this manner, over pressurization relief apparatus 1 prevents over pressurization of the pressure infusion bag. As will be shown in greater detail, the over pressurization limit at which pressure responsive mechanism 3 begins to exhaust pressurization is selected utilizing an over pressurization limit selector 4.

Figure 2C:
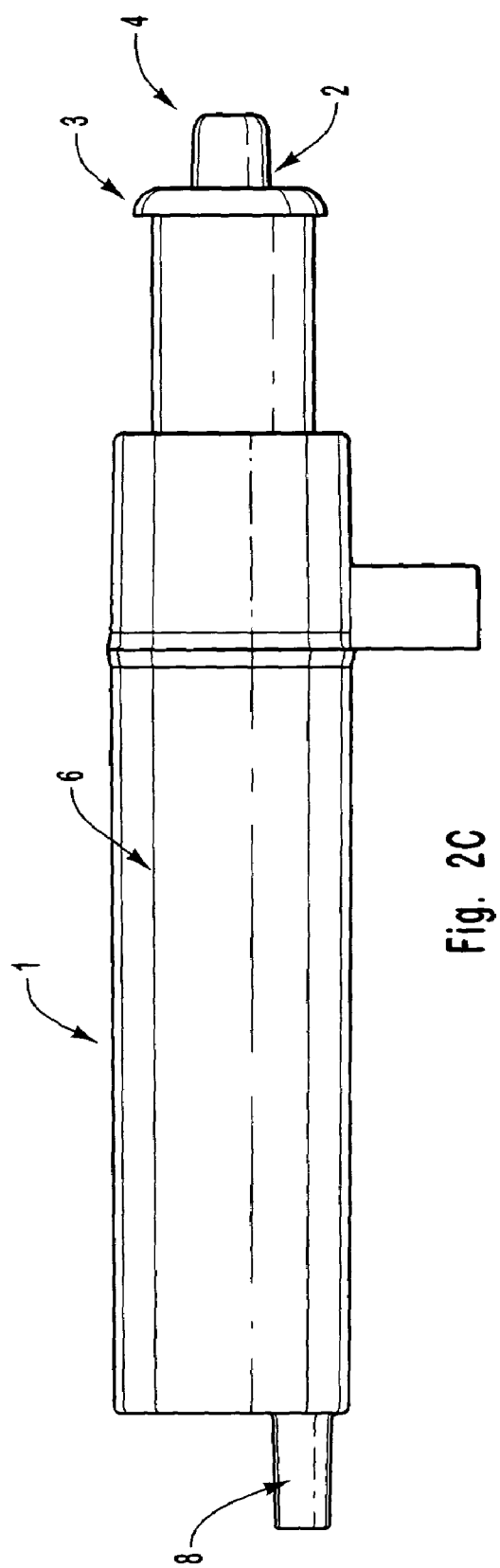
FIG. 2C illustrates the over pressurization relief apparatus where the pressurization in the pressure infusion bag has reached a second over pressurization

FIG. 2C illustrates an over pressurization relief apparatus 1 at a point in which the pressurization in the pressure infusion bag corresponds with a second over pressurization limit. In the illustrated embodiment, over pressurization limit selector 4 is in a second depressed position 4. The second depressed position corresponds with the selected second over pressurization limit. Pressure responsive mechanism 3 is in a third extended position corresponding with greater pressurization of the second over pressurization limit.

FIG. 3A is a cross-sectional view of over pressurization relief apparatus 1 illustrating valve mechanism 2 in greater detail. As previously discussed, over pressurization relief apparatus 1 comprises a valve mechanism 2, an outer housing 6, a tube engagement port 8, and a pressurization chamber 10. Valve mechanism 2 is positioned internal to outer housing 6. Valve mechanism 2 comprises a pressure responsive mechanism 3 and an over pressurization limit selector 4.

In the illustrated embodiment, pressure responsive mechanism 3 comprises an outer core 300, a spring element 310, and a spring retention member 320. Outer core 300 moves relative to outer housing 6 in response to changes in pressurization of the pressure infusion bag. Pressurization chamber 10 is in fluid communication with the pressure infusion bag. The changes in pressurization of the pressure infusion bag are conveyed to pressurization chamber 10 resulting in movement of outer core 300.

Spring element 310 circumscribes outer core 300 and provides a predetermined amount of resistance against movement of outer core 300. Once the pressurization in pressurization chamber 10 is sufficient to overcome the resistance of spring element 310, outer core 300 moves in response to subsequent changes in pressurization. Spring retention member 320 is coupled to outer core 300 and provides a surface for retaining spring element 310. The opposing end of spring retention member 310 is retained by outer housing 6. As the pressurization in pressurization chamber 10 increases the differential in pressurization between pressurization chamber 10 and the external environment results in movement of outer core 300 relative to outer housing 6. As outer core 300 moves in a distal direction, the displacement between spring retention member 320 and the distal end of outer housing 6 decreases and spring element 310 is compressed between outer housing 6 and spring retention member 320. As the displacement continues to decrease, spring element 310 is further compressed which results in a greater compressive force being exerted against spring retention member 320 by spring element 310.

The amount of biasing force provided by spring element 310 is selected to result in a predetermined amount of displacement of outer core 300 for each level of pressurization in pressurization chamber 10. As will be discussed in greater detail with reference to FIG. 4A, when the predetermined displacement of outer core 300 is reached, pressurization in the pressurization chamber 10 and the pressure infusion bag is relieved through a pressure relief mechanism. This limits the pressurization in pressurization chamber 10 and the pressure infusion bag to a predetermined over pressurization limit.

Outer core 300 includes an annular flange 302 and a recess 304. Annular flange 302 is positioned external to outer housing 6 to maintain the positioning of the distal end of outer core and over pressurization limit selector 4 relative to outer housing 6. Recess 304 provides a mechanism for coupling spring retention member 320 to outer core 300. Recess 304 includes a groove 306 for engaging an annular ridge of spring retention member 320. The groove/ridge combination of recess 304 and spring retention member 320 facilitates quick and easy connection of outer core 300 to spring retention member 320. Spring element 310 is positioned between spring retention member 320 and the portion of outer housing 6 adjacent annular flange 302. Spring element 310 is one example of a biasing member. As will be appreciated by those skilled in the art a variety of types and configurations of pressure responsive mechanisms can be utilized without departing from the scope and spirit of the present invention. For example, in one embodiment the pressure response and mechanism does not extend distally from outer housing. In another embodiment pressure responsive mechanism 3 utilizes a biasing member providing a tensile biasing force instead of a compressive biasing force.

Over pressurization selector 4 is positioned internal to pressure responsive mechanism 3. Over pressurization selector 4 comprises a selector assembly 20 and a seal assembly 50. Selector assembly 20 allows the user to select between one or more over pressurization limits. Seal assembly 50 provides an air tight seal ensuring that the air pressure in pressurization chamber 10 corresponds with the pressure in pressure infusion bag 5.

Selector assembly 20 is positioned internal to the distal portion of outer core 300. Selector assembly 20 comprises a plunger 200, a rotating member 210, an engagement member 220, an extension core 240, and a spring element 250. Plunger 200 contacts and is circumscribed by annular flange 302 of outer core 300. Plunger 200 provides a mechanism allowing a user to manually select from at least a first and second over pressurization limit. A user depresses plunger 200 to change from one over pressurization limit to a different over pressurization limit.

Rotating member 210 is positioned adjacent plunger 200. Rotating member cooperatively interacts with other components of selector assembly 200 to change the over pressurization limit. Rotating member 210 is moved proximally and distally by iteratively depressing and releasing plunger 200. Engagement member 220 is coupled to the internal surface of outer core 300. Engagement member 220 is cooperatively engaged by rotating member 210 such that rotating member 210 is moved proximally and distally relative to engagement member 220. Engagement member 220 assists in maintaining at least a first and second position of rotating member 210 corresponding with at least a first and second over pressurization limit of the pressurization chamber 10.

Extension core 240 is positioned adjacent to rotating member 210 so as to be directly engaged by rotating member 210 to change the displacement of extension core 240 relative to outer core 300. When a user depresses plunger 200, rotating member 210 moves in a proximal direction along with extension core 240. Spring element 250 is positioned external to extension core 240 such that when extension core 240 moves in a proximal direction, spring element 250 is compressed. Biasing force provided by spring element 250 maintains contact between extension core 240 and rotating member 210 to prevent change of the over pressurization limit until a subsequent depression and release of plunger 200.

Extension core 240 includes an enlarged end portion 242 for retaining spring element 250 and seal support connect connector void 246 for securing seal assembly 50 to selector assembly 20. Enlarged end portion 242 includes a tapered end surface 243 and a ridge 244. Tapered end surface 243 is directly engaged by rotating member 210. Ridge 244 retains one end of spring element 250. Seal support connector void 246 provides a mechanism for coupling seal assembly 50 to selector assembly 20.

Spring element 250 circumscribes extension core 240. Spring element 250 is retained between ridge 244 of extension core 240 and spring retention member 320 of outer core 300. When extension core 240 is moved in the proximal direction relative to outer core 300, the displacement between ridge 244 and spring retention member 320 is reduced resulting in compression of spring element 250. Compression of spring element 250 increases the biasing force exerted by spring element 250 on ridge 244 and spring retention member 320.

The positioning of extension core 240 is facilitated by rotating member 210 and spring element 250. In the illustrated embodiment, rotating member 210 and spring element 250 exert forces on opposing ends of enlarged end portion 242 to maintain positioning of extension core 240. Rotating member 210 cooperatively engages engagement member 220 to counteract the forces exerted by spring element 250 on enlarged end portion 242 and to maintain extension core 240 in a proximal position. When rotating member 210 is moved such that rotating member can slide distally to engagement member 220, the force exerted on ridge 244 of enlarged end portion 242 by spring element 250 results in movement of extension core 240 to a distal position.

Seal assembly 50 is coupled to seal support connector void 246 of extension core 240. Seal assembly 50 provides an air tight seal ensuring that the pressurization in pressurization chamber 10 corresponds with the pressurization in pressure infusion bag 5. Seal assembly 50 comprises a moveable seal. Seal assembly 50 provides an air tight seal between the pressurization chamber and a pressure relief groove in outer housing 6 when the pressurization in the pressurization chamber is less than the over pressurization limit. When the pressurization in the pressurization chamber is increased to greater than a selected over pressurization limit, the seal assembly 50 moves to a position in which the pressurization chamber is in fluid contact with the pressure relief groove such that the pressurization is exhausted from the pressurization chamber. When the pressurization is exhausted the pressurization in the pressurization chamber is maintain at the selected over pressurization limit.

Seal assembly 50 is coupled to selector assembly 20 such that seal assembly 50 is positioned proximally to selector assembly 20. Seal assembly 50 comprises a resilient seal 500 and a seal support 510. In the illustrated embodiment, resilient seal 500 comprises an elastomeric member or other flexible seal providing an air tight seal to pressurization chamber 10. Seal support 510 is coupled to extension core 240 and to resilient seal 500. Seal support 510 provides rigidity to maintain the uniform shape of resilient seal 500 and air tight seal created by resilient seal 500. Seal assembly 50 moves in proximal and distal direction in response to proximal and distal movement of extension core 240.

Outer housing 6 circumscribes other components of over pressurization relief apparatus 1 including outer core 300, extension core 240, and seal assembly 50. In the illustrated embodiment, outer housing 6 comprises a body member 600 and an end cap 610. Body member 600 is positioned proximally to end cap 610. Body member 600 and end cap 610 are connected after assembly and placement of valve mechanism 2. In this manner valve mechanism 2 can be positioned internal to outer housing 6 in a simple and efficient manner.

In the illustrated embodiment, plunger 200, engagement member 220, extension core 240, and seal assembly 50 are positioned at a distal position with respect to outer core 300. This results from the position of rotating member 210 relative to engagement member 220. Additionally, pressure responsive mechanism 3 is positioned at a proximal position with respect to outer housing 6. The position of pressure responsive mechanism 3 indicates that the pressure differential between pressurization chamber 10 and the external environment is insufficient to cause compression of spring element 310. This reflects a pressurization of the pressure infusion bag far below the selected over pressurization limit.

FIG. 3B illustrates plunger 200, rotating member 210, extension core 240, and seal assembly 50 positioned at a proximal position relative to outer core 300. In particular, seal assembly 50 is configured such that pressurization chamber 10 is smaller than that illustrated in FIG. 3A. The position of seal assembly 50 results from interaction between rotating member 210 and engagement member 220. Engagement member 220 maintains seal assembly 50 at the illustrated proximal position by maintaining rotating member 210 and thus extension core 240 at their respective proximal positions. Pressure responsive mechanism 3 continues to be positioned at its proximal most position with respect to outer housing 6. As explained with respect to FIG. 3A, the positioning of pressure responsive mechanism is due to the fact that the differential between the pressurization in the pressurization chamber 10 and the external environment is insufficient to cause compression of spring element 310.

The proximal position of seal assembly 50 corresponds with a greater effective length of over pressurization limit selector 4. The greater effective length of over pressurization limit selector 4 requires seal assembly 50 to be moved a greater distance to allow pressurization chamber 10 to be exhausted by pressure relief mechanism (i.e. pressure relief groove of FIG. 4A). In like manner, outer core 300 of pressure responsive mechanism 3 will also be moved a greater amount in the distal direction than when seal assembly 50 is positioned in a more distal position such as that shown in FIG. 3A.

In order for outer core 300 to move to a greater distal displacement relative to outer housing 6, spring retention member 320 must be moved closer to the distal end of outer housing 6. This results in greater compression of spring element 310 resulting in a greater compressive force being exerted on spring retention member 320 and the distal end of outer housing 6 by spring element 310. To overcome the compressive force provided by spring element 310 a greater pressurization differential must be created between pressurization chamber 10 and the external environment. As a result, depression of plunger 200 results in a greater pressurization of pressurization chamber 10 at the point in which the seal assembly 50 is moved to a sufficiently distal position to exhaust of air pressure for pressurization chamber 10 through the pressure relief mechanism. Thus, retention of rotating member 210 in a proximal position relative to engagement member 220 results in the setting of a higher over pressurization limit than when rotating member 210 is positioned in a distal location relative to engagement member 220.

Figure 4B:
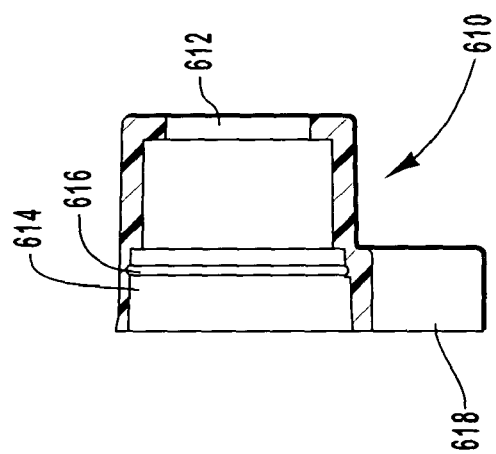
FIG. 4B is a cross-sectional side view of the end cap of the over pressurization relief apparatus according to one aspect of the present invention.
Figure 4A:
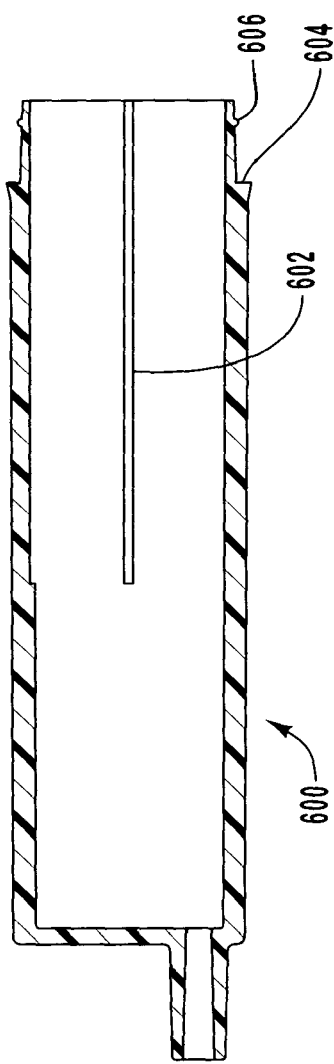
FIG. 4A is a cross-sectional side view of the body member of the over pressurization relief apparatus according to one aspect of the present invention.

FIG. 4A is a cross-sectional view of body member 600 illustrating pressure relief groove 602. In the illustrated embodiment body member 600 includes pressure relief groove 602, coupling portion 604, and annular ridge 606. Pressure relief groove 602 comprises a groove on the internal surface of body member 600. Pressure relief groove 602 extends from the distal end of body member 600 a predetermined distance along the length of body member 600. The length of pressure relief groove 602 is selected to correspond with desired over pressurization limits of the pressure infusion bag. Specifically, the length of pressure relief groove is such that a desired pressurization is reached in the pressurization chamber 10 when spring element 310 is sufficiently compressed to position seal assembly 50 so as to allow pressure relief groove 602 to exhaust pressurization chamber 10. Pressure relief groove 602 is one example of a pressure relief mechanism. A variety of types and configurations of pressure relief mechanisms can be utilized without departing from the scope and spirit of the present invention. For example in one embodiment, two or more pressure relief grooves are utilized to select a first and second over pressurization limit. In alternative embodiment, the pressure relief mechanism comprises one or more apertures positioned in body member 600 at specified positions allowing a user to select a first and second over pressurization limit.

Coupling portion 604 allows body member 600 to be coupled to end cap 610. Coupling portion 604 has an outer diameter that is smaller than the external diameter of other portions of body member 600. Coupling portion 604 includes an annular ridge 606. Annular ridge 606 is adapted to cooperatively engage an annular groove in end cap 610 to provide quick and efficient assembly with end cap 610.

FIG. 4B illustrates end cap 610 in greater detail. End cap 610 includes a plunger bore 612, an engagement aperture 614, and a tube retention member 618. Plunger bore 612 accommodates the distal end of outer core 300 of pressure responsive mechanism 3. Engagement aperture 614 is positioned proximally to plunger bore 612. Engagement aperture 614 has an inner diameter that is adapted to accommodate the outer diameter of coupling portion 604 of body member 600. Engagement aperture 614 allows body member 600 and end cap 610 to be coupled together. Engagement aperture 614 includes an annular groove 616. Annular groove 616 cooperatively engages annular ridge 606 of body member 600 to provide a mechanism for coupling body member 600 and end cap 610.

Tube retention member 618 provides a mechanism for securing the pneumatic tubing that connects the over pressurization relief apparatus with the pressure infusion bag. As will be appreciated by those skilled in the art a variety of types and configurations of coupling between body member 600 and end cap 610 can be utilized without departing from the scope and spirit of the present invention. For example, in one embodiment, a threaded coupling can be provided. In alternative embodiment, an adhesive is used to couple body member 600 with end cap 610.

Figure 5:
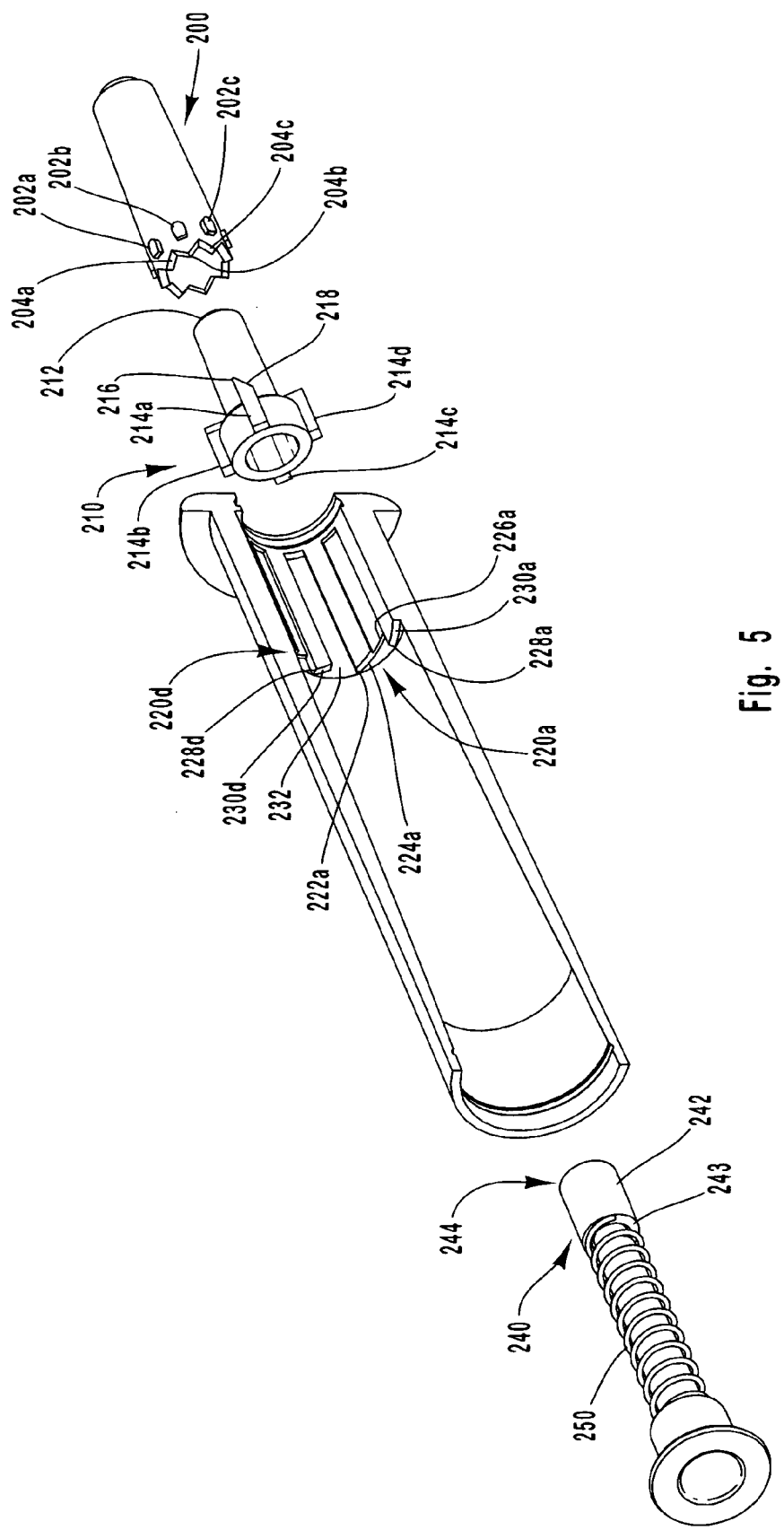
FIG. 5 is an exploded view of the internal components of the over pressurization relief apparatus according to one aspect of the present invention.

FIG. 5 illustrates over pressurization selector 4 in greater detail. There is shown an exploded view of over pressurization selector 4 including a cut away view of outer core 300 illustrating engagement member in greater detail. In the illustrated embodiment plunger 200 includes a plurality of projections 202a–n and plurality of teeth 204a–n. Projections 202a–n are positioned at the proximal end of the outer diameter of plunger 200. Projections 202a–n engage the internal surface of outer core 300 to prevent rotation of plunger 200. Teeth 204a–n are positioned on the bottom end of plunger 200, teeth 204a–c, engage rotating member 210 to facilitate proximal and distal positioning of rotating member. In particular, teeth 204a–n interact with rotating member 210 to provide displacement and an initial rotation of rotating member 210 relative to engagement member 220. Teeth 204a–n allows rotating member 210 to move proximally and distally with respect to outer core 300. As will be understood by those skilled in the art, a variety of mechanisms can be utilized to prevent rotation of plunger 200 and is not limited to projections 202. Additionally, it will be understood that any number of teeth or other similar mechanisms can be used to promote rotation of rotating member 210.

Rotating member 210 comprises an insertion end 210 and rotation members 214a, b, c, d. Insertion end 210 is positioned at the distal end of rotating member 210 and is configured to be positioned internal to plunger 200. This allows teeth 204a–c of plunger 200 to engage rotation members 214 of rotating member 210. Each of rotation members 214 include a ridge 216 and a helical ramp 218. Ridges 216 are positioned on the top edge at one side of rotation members 214. Ridges 216 promote rotation of rotating member 210 in a desired direction. Helical ramps 218 also promote rotation of rotating member 210. When teeth 204a–c of plunger 200 engage helical ramp 218 of rotating member 210, ridge 216 minimizes rotation of rotating member in other than the desired direction. In the preferred embodiment, teeth 204a–c also have a helical configuration to facilitate direct surface contact between 204a–c and helical ramps 218a–c. As teeth 204a–c of plunger 200 exert additional pressure on helical ramps 218a–c, helical ramps 218a–c slide relative to the side portions of teeth 204a–c. This causes rotation of rotating member 210.

Engagement member 220 comprises a first engagement ridge 222, a first helical ramp 224, an extension engagement notch 226, a second engagement ridge 228, a second helical ramp 230, and a channel 232. First engagement ridge 222 provides a mechanism for facilitating rotation of rotating member 210 in the desired direction. First helical ramp 224 is positioned adjacent to first engagement ridge 222. First helical ramp 224 engages ridge 216 and helical ramp 218 of rotation members 214. As tapered end surface 244 exerts pressure against rotating member 210 as a result of biasing of spring element 250, the direction and configuration of helical ramp 218 and first helical ramp 224 causes rotation of rotating member 210. Extension engagement notch 226 is positioned at the end of first helical ramp 224. Extension engagement notch 226 is adapted to engage ridge 216 of rotation member 214 of rotating member 210 to prevent further rotation of rotating member 210. This secures rotating member 210 in a proximal position relative to engagement member 220.

A second engagement ridge 228 is positioned adjacent extension engagement notch 226. When a user depresses plunger 200, teeth 204a–c engage rotation members 214 of rotating member 210. Plunger 200 pushes rotating member 210 to a proximal position while teeth 204a–c engage helical ramp 218 of rotation members 214 causing a small initial rotation of rotating member 210. The small initial rotation of rotating member 210 aligns ridges 216a–c at a position slightly past second engagement ridge 228. Second helical ramp 230 is positioned adjacent second engagement ridge 228.

As the user releases plunger 200, rotating member 210 is pushed in a distal direction by the biasing of spring element 250. Rotating member 210 is forced in a distal direction, and ridges 216a–c engage second engagement ridges 228a–c of engagement member 220. Additional distal movement resulting from biasing of spring element 250 causes ridge 216 and helical ramp 218 of rotation members 214 to engage rotating member 210 resulting in rotation of rotating member 210 along second engagement ridge 228.

A channel 232 is positioned adjacent to helical ramp 230. As ridge 216 of rotation member 214 rotates to the edge of second helical ramp 230, ridge 216 passes into channel 232 followed by helical ramp 218 and finally all of rotation member 214. As rotation member 214 passes into channel 232, rotating member 210 moves distally to engagement member 220. In the illustrated embodiment, four rotation members 214 are positioned on rotating member 210. Corresponding with the four rotation members 214 of rotating member 210, four channel members 232 and four extension engagement notches 226 are provided on engagement member 220. Thus each of rotation members 214 engage each of the four extension engagement notches 226 when rotating member 210 is secured in a proximal position by engagement member 220. Alternatively each of the four rotation members 214 are allowed to pass through the four channels 232 to permit rotating member 210 to be positioned distally to engagement member 220.

In the illustrated embodiment, plunger 200 includes eight teeth 204. This is due to the fact that plunger 200 is prevented from rotating by projections 202. Thus the eight teeth 204 are positioned to contact rotation members 214 notwithstanding the positioning of the rotation members 214. This allows teeth 204 to contact rotation members 214 and provide an initial rotation to move past each of the four first engagement ridges 222 as well as the second engagement ridges 228. The configuration of engagement member 220 in the illustrated embodiment permits the user to quickly and efficiently toggle between a first and second predetermined over pressurization limit. In the embodiment, the first over pressurization limit is associated with a distal position of rotating member 210 such that rotation members 214 are positioned in channels 232 and second over pressurization limit corresponds with a proximal position of rotating member 210 such that rotation members 214 are positioned adjacent extension engagement notches 226. As will be appreciated by those skilled in the art, a variety of types and configurations of engagement members and rotating members can be utilized to provide more than a first and second over pressurization limit.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A pressure infusion apparatus comprising:
   a pressure infusion bag being filled with a medium for exerting pressure on an infusate bag; and
   a manually operable over pressurization relief apparatus linked to the pressure infusion bag, the manually operable over pressurization relief apparatus allowing the user to quickly and efficiently toggle between at least a first and second predetermined over pressurization limit, the selected over pressurization limit corresponding to an over pressurization limit of the medium in the pressure infusion bag.

2. The pressure infusion apparatus of claim 1, wherein the medium in the pressure infusion bag comprises a liquid.

3. The pressure infusion apparatus of claim 1, wherein the medium in the pressure infusion bag comprises a gas.

4. The pressure infusion apparatus of claim 3, wherein the medium in the pressure infusion bag comprises ambient air.

5. The pressure infusion apparatus of claim 4, wherein the manually operable over pressurization relief apparatus includes a pressurization chamber.

6. The pressure infusion apparatus of claim 5, wherein the pressurization chamber is fluid coupled to the pressure infusion bag.

7. The pressure infusion apparatus of claim 6, wherein the pressurization in the pressurization chamber corresponds with the pressurization in the pressure infusion bag.

8. The pressure infusion apparatus of claim 7, wherein the manually operable over pressurization relief apparatus includes a manual over pressurization selector.

9. The pressure infusion apparatus of claim 8, wherein the manual overpressureization selector allows the user to quickly and efficiently toggle between at least a first and second predetermined over pressurization limit.

10. The over pressurization relief apparatus of claim 1, wherein the movable seal comprises a portion of a valve mechanism.

11. The over pressurization relief apparatus of claim 10, wherein the valve mechanism further comprises a pressure responsive mechanism and an over pressurization selector.

12. The over pressurization relief apparatus of claim 11, wherein the over pressurization selector moves relative to the pressure responsive mechanism to change the amount of pressurization in the pressurization required to move the seal in fluid contact with the pressure relief groove.

13. The over pressurization relief apparatus of claim 12, wherein the over pressurization selector includes a plunger, a rotating member, and an engagement member to maintain the over pressurization selector in at least a first position and at least a second position.

14. The over pressurization relief apparatus of claim 13, wherein the rotating member moves relative to the engagement member to allow the over pressurization selector to move relative to the pressure responsive mechanism.

15. The over pressurization relief apparatus of claim 14, wherein the rotating member includes a plurality of rotation members, each rotation member having a ridge and a helical ramp and wherein each the engagement member includes a plurality of first engagement ridges, first helical ramps, extension engagement notches, second engagement ridges, second helical ramps, and channels wherein the ridges and ramps of the rotation members engage the extension engagement notches to when at a higher over pressurization limit and the rotation members are positioned in the channels when at a lower over pressurization limit.

* * * * *

UNITED STATES PATENT AND TRADEMARK OFFICE
CERTIFICATE OF CORRECTION

| | | |
|---|---|---|
| PATENT NO. | : 6,966,893 B2 | Page 1 of 2 |
| APPLICATION NO. | : 10/649001 | |
| DATED | : November 22, 2005 | |
| INVENTOR(S) | : Troy Holtby et al. | |

It is certified that error appears in the above-identified patent and that said Letters Patent is hereby corrected as shown below:

Column 2,
Line 18, before "pressure infusion" insert -- a --.

Column 3,
Line 6, after "pressurization" insert -- limit. --.

Column 8,
Line 23, change "maintain" to -- maintained --.

Column 9,
Line 13, before "pressure relief" insert -- a --.
Line 32, before "air pressure" delete "of".
Line 60, after "In" insert -- an --.

Column 10,
Lines 38, 55, 62 and 65, change "204$a$-$c$" to -- 204$a$-$n$ --.
Line 43, change "allows" to -- allow --.
Line 47, change "is" to -- are --.
Lines 51 and 52, change "210" to -- 212 --.
Line 64, before "in other" insert -- 210 --.
Line 66, after "between" insert -- teeth --.
Line 67, before "and helical" change "204$a$-$c$" to -- 204$a$-$n$ --.
Line 67, change "218$a$-$c$" to -- 218 --.
Line 67, after "teeth" change "204$a$-$c$" to -- 204 $a$-$n$ --.

UNITED STATES PATENT AND TRADEMARK OFFICE
CERTIFICATE OF CORRECTION

PATENT NO. : 6,966,893 B2
APPLICATION NO. : 10/649001
DATED : November 22, 2005
INVENTOR(S) : Troy Holtby et al.

It is certified that error appears in the above-identified patent and that said Letters Patent is hereby corrected as shown below:

Column 11,
Line 2, change "218*a-c*, helical ramps 218 *a-c*" to -- 218, helical ramps 218 --.
Lines 3, 26 and 28, change "204*a-c*" to -- 204 *a-n* --.
Lines 31 and 38, change "216 *a-c*" to -- 216 --.
Line 38, change "218*a-c*" to -- 218 --.

Column 14,
Line 10, after "notches" delete "to".

Signed and Sealed this

Eighteenth Day of July, 2006

JON W. DUDAS
*Director of the United States Patent and Trademark Office*